US006333187B1

(12) United States Patent
Beekwilder et al.

(10) Patent No.: US 6,333,187 B1
(45) Date of Patent: Dec. 25, 2001

(54) **COLLECTION OF PHAGEMIDS, AND A COLLECTION OF *E. COLI* CELLS CARRYING THE PHAGEMIDS**

(75) Inventors: Jules Beekwilder, Wageningen (NL); Jasna Rakonjac, New York, NY (US); Dirk Bosch, Wageningen (NL); Maarten Jongsma, Wageningen (NL); Willem Stiekema, Wageningen (NL); Goran Jovanovic, New York, NY (US)

(73) Assignee: Centrum Voor Plantenveredelings-en, Wageningen (NL)

( * ) Notice: Subject to any disclaimer, the term of this patent is extended or adjusted under 35 U.S.C. 154(b) by 0 days.

(21) Appl. No.: 09/163,540

(22) Filed: Sep. 30, 1998

(51) Int. Cl.[7] .............................. C12N 1/21; C12N 15/63; C12N 15/31
(52) U.S. Cl. .................................. 435/252.33; 435/320.1; 536/23.4; 536/23.7; 536/24.1
(58) Field of Search .......................... 435/320.1, 252.33; 536/23.4, 23.7, 24.1

*Primary Examiner*—John S. Brusca
(74) *Attorney, Agent, or Firm*—Smith, Gambrell & Russell, LLP

(57) ABSTRACT

The invention relates to phagemid vectors comprising
  i) a promoter operatively linked to a gene coding for a translational fusion between a peptide and a filamentous single strand DNA bacteriophage coat protein or a part thereof, which promoter is induced by expression of gene IV of a filamentous bacteriophage,
  ii) a replication origin derived from a filamentous single strand DNA bacteriophage, and
  iii) a plasmid replication origin.

Figure 2:
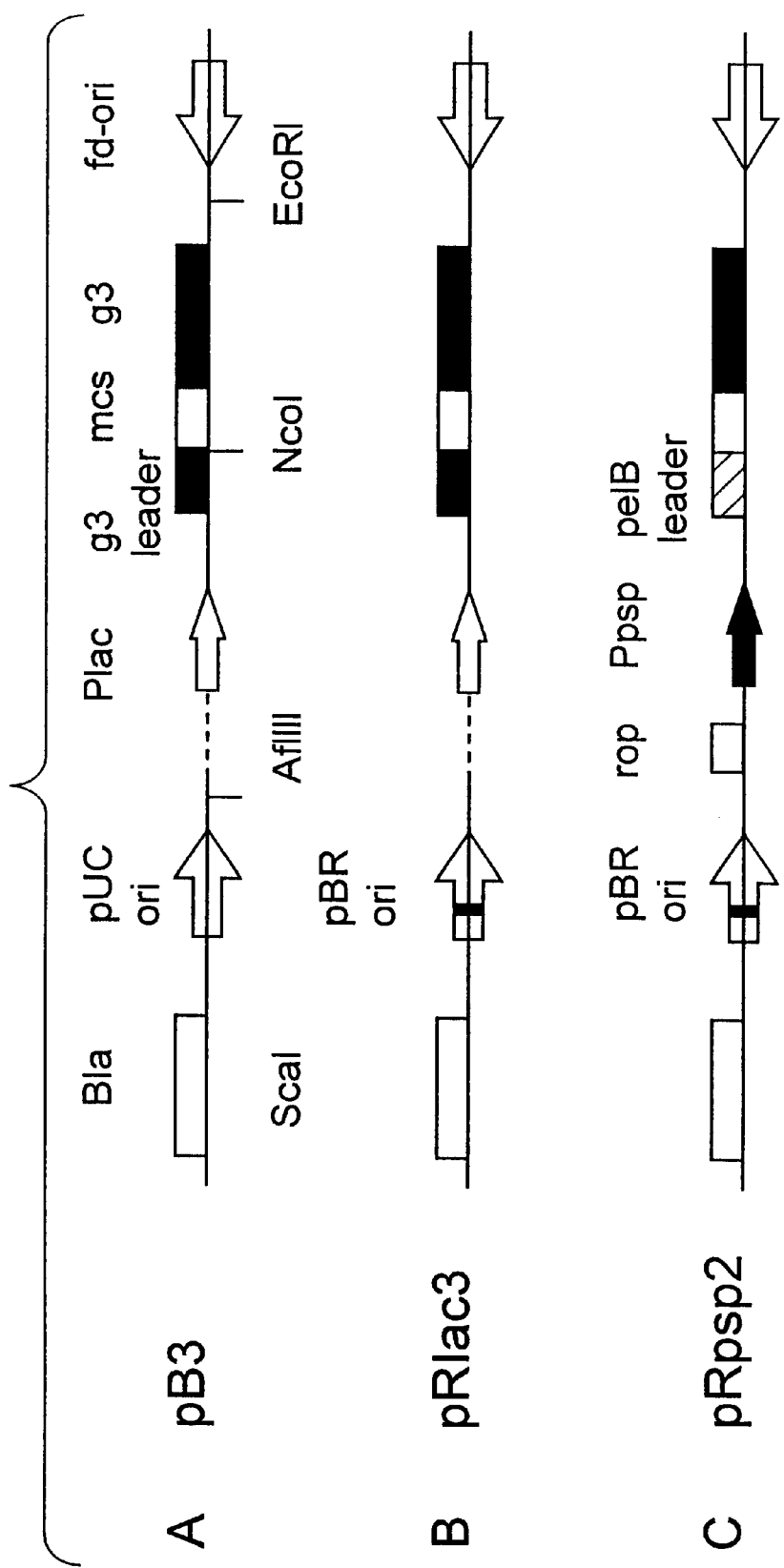

Further the invention relates to *E. coli* cells representing the phagemids. The phagemid vectors are suitable for phage display.

19 Claims, 7 Drawing Sheets

FIG. 1

Wild type PI2
```
        Cys Thr Leu Glu Cys         Cys Pro Arg Asn Cys
——————— TGC ACT TTA GAA TGT ——————— TGC CCG CGA AAT TGC ———————
```

PI2 library
```
        Cys Ala Ala Ala Cys         Cys Xxx Xxx Xxx Cys
——————— TGC GCC GCG GCA TGT ——————— TGC NNK NNK NNK TGC ———————
```

FIG. 5A

```
   1 GACGAAAGGGCCTCGTGATACGCCTATTTTTATAGGTTAATGTCATGATA
  51 ATAATGGTTTCTTAGACGTCAGGTGGCACTTTTCGGGGAAATGTGCGCGG
 101 AACCCCTATTTGTTTATTTTTCTAAATACATTCAAATATGTATCCGCTCA
 151 TGAGACAATAACCCTGATAAATGCTTCAATAATATTGAAAAAGGAAGAGT
 201 ATGAGTATTCAACATTTCCGTGTCGCCCTTATTCCCTTTTTGCGGCATT
 251 TTGCCTTCCTGTTTTTGCTCACCCAGAAACGCTGGTGAAAGTAAAAGATG
 301 CTGAAGATCAGTTGGGTGCTCGAGTGGGTTACATCGAACTGGATCTCAAC
 351 AGCGGTAAGATCCTTGAGAGTTTTCGCCCCGAAGAACGTTTTCCAATGAT
 401 GAGCACTTTTAAAGTTCTGCTATGTGGCGCGGTATTATCCCGTATTGACG
 451 CCGGGCAAGAGCAACTCGGTCGCCGCATACACTATTCTCAGAATGACTTG
 501 GTTGAGTACTCACCAGTCACAGAAAAGCATCTTACGGATGGCATGACAGT
 551 AAGAGAATTATGCAGTGCTGCCATAACCATGAGTGATAACACTGCGGCCA
 601 ACTTACTTCTGACAACGATCGGAGGACCGAAGGAGCTAACCGCTTTTTTG
 651 CACAACATGGGGGATCATGTAACTCGCCTTGATCGTTGGGAACCGGAGCT
 701 GAATGAAGCCATACCAAACGACGAGCGTGACACCACGATGCCTGCAGCAA
 751 TGGCAACAACGTTGCGCAAACTATTAACTGGCGAACTACTTACTCTAGCT
 801 TCCCGGCAACAATTAATAGACTGGATGGAGGCGGATAAAGTTGCAGGACC
 851 ACTTCTGCGCTCGGCCCTTCCGGCTGGCTGGTTTATTGCTGATAAATCTG
 901 GAGCCGGTGAGCGTGGGTCTCGCGGTATCATTGCAGCACTGGGGCCAGAT
 951 GGTAAGCCCTCCCGTATCGTAGTTATCTACACGACGGGGAGTCAGGCAAC
1001 TATGGATGAACGAAATAGACAGATCGCTGAGATAGGTGCCTCACTGATTA
1051 AGCATTGGTAACTGTCAGACCAAGTTTACTCATATATACTTTAGATTGAT
1101 TTAAAACTTCATTTTTAATTTAAAAGGATCTAGGTGAAGATCCTTTTTGA
1151 TAATCTCATGACCAAAATCCCTTAACGTGAGTTTTCGTTCCACTGAGCGT
1201 CAGACCCCGTAGAAAAGATCAAAGGATCTTCTTGAGATCCTTTTTTTCTG
1251 CGCGTAATCTGCTGCTTGCAAACAAAAAAACCACCGCTACCAGCGGTGGT
1301 TTGTTTGCCGGATCAAGAGCTACCAACTCTTTTTCCGAAGGTAACTGGCT
1351 TCAGCAGAGCGCAGATACCAAATACTGTCCTTCTAGTGTAGCCGTAGTTA
1401 GGCCACCACTTCAAGAACTCTGTAGCACCGCCTACATACCTCGCTCTGCT
1451 AATCCTGTTACCAGTGGCTGCTGCCAGTGGCGATAAGTCGTGTCTTACCG
1501 GGTTGGACTCAAGACGATAGTTACCGGATAAGGCGCAGCGGTCGGGCTGA
1551 ACGGGGGGTTCGTGCACACAGCCCAGCTTGGAGCGAACGACCTACACCGA
1601 ACTGAGATACCTACAGCGTGAGCTATGAGAAAGCGCCACGCTTCCCGAAG
1651 GGAGAAAGGCGGACAGGTATCCGGTAAGCGGCAGGGTCGGAACAGGAGAG
1701 CGCACGAGGGAGCTTCCAGGGGGAAACGCCTGGTATCTTTATAGTCCTGT
1751 CGGGTTTCGCCACCTCTGACTTGAGCGTCGATTTTTGTGATGCTCGTCAG
1801 GGGGGCGGAGCCTATGGAAAAACGCCAGCAACGCGGCCTTTTTACGGTTC
1851 CTGGCCTTTTGCTGGCCTTTTGCTCACATGTTCTTTCCTGCGTTATCCCC
1901 TGATTCTGTGGATAACCGTATTACCGCCTTTGAGTGAGCTGATACCGCTC
1951 GCCGCAGCCGAACGACCGAGCGCAGCGAGTCAGTGAGCGAGGAAGCGGAA
2001 GAGCGCCTGATGCGGTATTTTCTCCTTACGCATCTGTGCGGTATTTCACA
2051 CCGCATATATGGTGCACTCTCAGTACAATCTGCTCTGATGCCGCATAGTT
```

FIG. 5B

```
2101 AAGCCAGTATACACTCCGCTATCGCTACGTGACTGGGTCATGGCTGCGCC
2151 CCGACACCCGCCAACACCCGCTGACGCGCCCTGACGGGCTTGTCTGCTCC
2201 CGGCATCCGCTTACAGACAAGCTGTGACCGTCTCCGGGAGCTGCATGTGT
2251 CAGAGGTTTTCACCGTCATCACCGAAACGCGCGAGGCAGCTGCGGTAAAG
2301 CTCATCAGCGTGGTCGTGAAGCGATTCACAGATGTCTGCCTGTTCATCCG
2351 CGTCCAGCTCGTTGAGTTTCTCCAGAAGCGTTAATGTCTGGCTTCTGATA
2401 AAGCGGGCCATGTTAAGGGCGGTTTTTTCCTGTTTGGTCACTGATGCCTC
2451 CGTGTAAGGGGATTTCTGTTCATGGGGGTAATGATACCGATGAAACGAG
2501 AGAGGATGCTCACGATACGGGTTACTGATGATGAACATGCCCGGTTACTG
2551 GAACGTTGTGAGGGTAAACAACTGGCGGTATGGATGCGGCGGGACCAGAG
2601 AAAAATCACTCAGGGTCAATGCCAGCGCTTCGTTAATACAGATGTAGGTG
2651 TTCCACAGGGTAGCCAGCAGCATCCTGCGATGCAGATCCGGAACATAATG
2701 GTGCAGGGCGCTGACTTCCGCGTTTCCAGACTTTACGAAACACGGAAACC
2751 GAAGACCATTCATGTTGTTGCTCAGGTCGCAGACGTTTTGCAGCAGCAGT
2801 CGCTTCACGTTCGCTCGCGTATCGGTGATTCATTCTGCTAACCAGTAAGG
2851 CAACCCCGCCAGCCTAGCCGGGTCCTCAACGACAGGAGCACGATCATGCG
2901 CACCCGTGGGGCCGCCATGCCGGCGATAATGGCCTGCTTCTCGCCGAAAC
2951 GTTTGGTGGCGGGACCAGTGACGAAGGCTTGAGCGAGGGCGTGCAAGATT
3001 CCGAATACCGCAAGCGACAGGCCGATCATCGTCGCGCTCCAGCGAAAGCG
3051 GTCCTCGCCGAAAATGACCCAGAGCGCTGCCGGCACCTGTCCTACGAGTT
3101 GCATGATAAAGAAGACAGTCATAAGTGCGGCGACGATAGTCATGCCCCGC
3151 GCCCACCGGAAGGAGCTGACTGGGTTGAAGGCTCTCAAGGGCATCGGTCG
3201 AGATCCCGGTGCCTAATGAGTGAGCTAACTTACATTAATTGCGTTGCGCT
3251 CACTGCCCGCTTTCCAGTCGGGAAACCTGTCGTGCCAGCTGCATTAATGA
3301 ATCGGCCAACGCGCGGGGAGAGGCGGTTTGCGTATTGGGCGCCAGGGTGG
3351 TTTTTCTTTTCACCAGTGAGACGGGCAACAGCTGATTGCCCTTCACCGCC
3401 TGGCCCTGAGAGAGTTGCAGCAAGCGGTCCACGCTGGTTTGCCCCAGCAG
3451 GCGAAAATCCTGTTTGATGGTGGTTAACCATGATGAATTCGCCACTTGT
3501 TAGTGTAATTCGCTAACTCATCCTGGCATGTTGCTGTTGATTCTTCAATC
3551 AGATCTTTATAAATCAAAAAGATAAAAATTGGCACGCAAATTGTATTAA
3601 CAGTTCAGCAGGACAATCCTGAACGCAGAAATCAAGAGGACAACATATGA
3651 AATACCTGCTGCCGACCGCTGCTGCTGGTCTGCTGCTCCTCGCTGCCCAG
3701 CCGGCGATGGCCATGGCCCAGGTGCAGCTGCAGGTCGACCTCGAGATCAA
3751 ACGGGCGGCCGCAGAACAAAAACTCATCTCAGAAGAGGATCTGAATGGGG
3801 CCGCATAGACTGTTGAAGTTGTTTAGCAAAACCTCATACAGAAAATTCA
3851 TTTACTAACGTCTGGAAAGACGACAAAACTTTAGATCGTTACGCTAACTA
3901 TGAGGGCTGTCTGTGGAATGCTACAGGCGTTGTGGTTTGTACTGGTGACG
3951 AAACTCAGTGTTACGGTACATGGGTTCCTATTGGGCTTGCTATCCCTGAA
4001 AATGAGGGTGGTGGCTCTGAGGGTGGCGGTTCTGAGGGTGGCGGTTCTGA
4051 GGGTGGCGGTACTAAACCTCCTGAGTACGGTGATACACCTATTCCGGGCT
4101 ATACTTATATCAACCCTCTCGACGGCACTTATCCGCCTGGTACTGAGCAA
4151 AACCCCGCTAATCCTAATCCTTCTCTTGAGGAGTCTCAGCCTCTTAATAC
4201 TTTCATGTTTCAGAATAATAGGTTCCGAAATAGGCAGGGTGCATTAACTG
```

FIG. 5C

```
4251 TTTATACGGGCACTGTTACTCAAGGCACTGACCCCGTTAAAACTTATTAC
4301 CAGTACACTCCTGTATCATCAAAAGCCATGTATGACGCTTACTGGAACGG
4351 TAAATTCAGAGACTGCGCTTTCCATTCTGGCTTTAATGAGGATCCATTCG
4401 TTTGTGAATATCAAGGCCAATCGTCTGACCTGCCTCAACCTCCTGTCAAT
4451 GCTGGCGGCGGCTCTGGTGGTGGTTCTGGTGGCGGCTCTGAGGGTGGCGG
4501 CTCTGAGGGTGGCGGTTCTGAGGGTGGCGGCTCTGAGGGTGGCGGTTCCG
4551 GTGGCGGCTCCGGTTCCGGTGATTTTGATTATGAAAAAATGGCAAACGCT
4601 AATAAGGGGGCTATGACCGAAAATGCCGATGAAAACGCGCTACAGTCTGA
4651 CGCTAAAGGCAAACTTGATTCTGTCGCTACTGATTACGGTGCTGCTATCG
4701 ATGGTTTCATTGGTGACGTTTCCGGCCTTGCTAATGGTAATGGTGCTACT
4751 GGTGATTTTGCTGGCTCTAATTCCCAAATGGCTCAAGTCGGTGACGGTGA
4801 TAATTCACCTTTAATGAATAATTTCCGTCAATATTTACCTTCTTTGCCTC
4851 AGTCGGTTGAATGTCGCCCTTATGTCTTTGGCGCTGGTAAACCATATGAA
4901 TTTTCTATTGATTGTGACAAAATAAACTTATTCCGTGGTGTCTTTGCGTT
4951 TCTTTTATATGTTGCCACCTTTATGTATGTATTTTCGACGTTTGCTAACA
5001 TACTGCGTAATAAGGAGTCTTAATAAGAATTCACTGGCCGTCGTTTTACA
5051 ACGTCGTGACTGGGAAAACCCTGGCGTTACCCAACTTAATCGCCTTGCAG
5101 CACATCCCCCTTTCGCCAGCTGGCGTAATAGCGAAGAGGCCCGCACCGAT
5151 CGCCCTTCCCAACAGTTGCGCAGCCTGAATGGCGAATGGCGCCTGATGCG
5201 GTATTTTCTCCTTACGCATCTGTGCGGTATTTCACACCGCATATAAATTG
5251 TAAACGTTAATATTTTGTTAAAATTCGCGTTAAATTTTTGTTAAATCAGC
5301 TCATTTTTTAACCAATAGGCCGAAATCGGCAAAATCCCTTATAAATCAAA
5351 AGAATAGCCCGAGATAGGGTTGAGTGTTGTTCCAGTTTGGAACAAGAGTC
5401 CACTATTAAAGAACGTGGACTCCAACGTCAAAGGGCGAAAAACCGTCTAT
5451 CAGGGCGATGGCCCACTACGTGAACCATCACCCAAATCAAGTTTTTTGGG
5501 GTCGAGGTGCCGTAAAGCACTAAATCGGAACCCTAAAGGGAGCCCCCGAT
5551 TTAGAGCTTGACGGGGAAAGCCGGCGAACGTGGCGAGAAAGGAAGGGAAG
5601 AAAGCGAAAGGAGCGGGCGCTAGGGCGCTGGCAAGTGTAGCGGTCACGCT
5651 GCGCGTAACCACCACACCCGCCGCGCTTAATGCGCCGCTACAGGGCGCGT
5701 ACTATGGTTGCTTTGACGGGTGCAGTCTCAGTACAATCTGCTCTGATGCC
5751 GCATAGTTAAGCCAGCCCCGACACCCGCCAACACCCGCTGACGCGCCCTG
5801 ACGGGCTTGTCTGCTCCCGGCATCCGCTTACAGACAAGCTGTGACCGTCT
5851 CCGGGAGCTGCATGTGTCAGAGGTTTTCACCGTCATCACCGAAACGCGCG
5901 A
```

COLLECTION OF PHAGEMIDS, AND A COLLECTION OF E. COLI CELLS CARRYING THE PHAGEMIDS

This invention relates to phagemid vectors suitable for phage display. Phage display is a tool to identify peptide variants with a particular binding specificity. Phage display comprises a collection of peptides. Each of these peptides is expressed on a filamentous bacteriophage particle as fusion to one of the coat proteins of single strand DNA phages like f1, fd and M13, and each of them is encoded by the corresponding DNA molecule inside that particle. By exposing the collection to a target, and selectively amplifying those members of the collection that bind to the target genes can be isolated encoding peptides that have binding affinity for the target. The principle of phage display is described extensively, for instance in U.S. Pat. No. 5,223,409. The variant binding peptides can for instance be derived from antibodies (Hoogenboom et al., 1991), proteinese inhibitors (Roberts et al., 1992), cDNAs (Jespers, 1995) or random peptides (Cwirla, 1991). The invention is also relevant for other selection procedures that involve phages like Selectively Infective Phage (SIP) and Selection and Amplification of Phage (SAP) as described by Duenas et al., 1994, Gramatikoff et al., 1995 and Krebber et al., 1995. The main power of phage display is rapid screening of vast numbers of variants.

Various cases of large libraries dominated by deletion mutants have been reported (Smiley & Benkovic, 1994; Tan et al., 1994; Bradbury, 1998). Such DNAs may easily appear in the course of alternating selection and phage amplification stages, since they reproduce much faster than intact phagemids. This may particularly be the case when the protein of interest is not indifferent to E.coli, but retards its growth (Krebber et al., 1996). Proteins may have toxic effects in their native fold, like in the case of lysozyme (Maenaka et al., 1996), or inhibit growth when aberrantly folded, as has been reported for some antibodies (Knappik & Pluckthun, 1996). A more general problem may be that already a low level of expression of the bacteriophage coat protein (g3p), to which the protein of interest is fused, retards growth of E. coli. In addition, g3p alters the properties of the E. coli outer membrane so that it can no longer be infected by helperphage (Boeke et al., 1982; Rakenjae et al., 1997).

The existing phagemid vector systems for phage display, most of them based on pHEN1 (Hoogenboom et al., 1991), generally use the promoter of the E. coli lac-operon. This system is preferred over the natural g3p promoter, since the lac-promoter can at least partially be repressed during library generation by addition of glucose, and induced during phage synthesis by removal of glucose. In spite of this control, several reports indicate a high incidence of deletion phages. The present inventors carried out some experiments to be described in the experimental part, which yielded only mutants that carry deletions or amber stopcodons.

To overcome the above problem Krebber et al. (1996) use a phagemid vector which carries the lacI repressor gene and a transcription termination signal just upstream of the lac-promoter. This provides improved control over the lac-promoter, as judged from Western blots and bacterial morphology.

EP 0.699.760 discloses a phagemid vector system for phage display which uses the lambda $P_L$-promoter and a bacterial strain carrying a lysogenic lambda phage. This patent application does not comprise a comparison to other systems neither are any advantages mentioned.

According to the present invention the above problem has been solved by a collection of phagemids comprising
i) a promoter operatively linked to a gene coding for a translational fusion between a peptide and a filamentous single strand DNA bacteriophage coat protein or a part thereof, which promoter is induced by expression of gene IV of a filamentous bacteriophage,
ii) a replication origin derived from a filamentous single strand DNA bacteriophage, and
iii) a plasmid replication origin.

Hereinafter the gene coding for a translational fusion between a peptide and a filamentous single strand DNA bacteriophage coat protein or a part thereof will be shortly referred to as the fusion gene. The fusion protein is encoded by this fusion gene.

According to the invention the commonly used lac promoter is replaced by a promoter which is repressed under normal growth conditions, and induced by expression of gene IV of a filamentous bacteriophage.

According to a preferred embodiment the promoter is the promoter of the E. coli phage-shock-protein (psp) operon or a homologous promoter from a different organism.

The psp-promoter comprises the region spanning 200 bp upstream of the E. coli pspA gene. The promoter is induced when gene IV of filamentous bacteriophages is expressed. The promoter is also triggered by expression of gene IV-protein homologues, like the pulD gene product of Klebsiella oxytoca. The actual mechanism of induction is not fully understood, but a proposed pathway is discussed in Model et al., 1997. The organization of the psp promoter is alike a sigma 54 promoter (reviewed in Morett et al., 1993). Sigma 54 promoters have been found in E.coli, Salmonella, Klebsiella, Rhizobium, Pseudomonas and Azotobacter species. It is therefore possible that psp promoters are present in these organisms, particularly in Salmonella typhimurium and Shigella spp. since these are closely related to E. coli.

The system using the above defined promoter has two technical advantages. Firstly, it provides satisfactory control over the encoded gene-fusions, as judged from superinfection levels, and growthcurves as well as in a complete phage display selection experiment. Secondly, handling procedures for switching on the promoter after helperphage infection, which normally involves delicate washing steps in order to remove glucose, are no longer required. This may for instance be important for large scale production of phage libraries in fermentor devices or in automated phage display procedures.

According to a further preferred embodiment of the invention the plasmid replication origin is a low-copynumber origin of replication. Preferably the low-copynumber origin of replication is derived from pBR322. Using this plasmid replication origin the phagemid copynumber is lowered to about 30 per cell, instead of about 500 as in the case of pUC-derived vectors like pB3 (Sambrook et al., 1989).

According to yet another preferred embodiment the phagemid comprises the rop gene from pBR322, which reduces the copynumber an additional twofold. The order of the various elements to be present on the phagemids of the invention is not critical, but preferably the phagemids comprise in a 5' to 3' direction: the plasmid replication origin and the promoter operatively linked to the fusion gene.

If the rop gene is present, it is suitably present between the plasmid replication origin and the promoter operatively linked to the fusion gene.

In a further preferred embodiment the promoter is operatively linked to the leader sequence of the polB gene of Erwinia carotovora and the fusion gene.

The phagemids of the invention generally comprise at least one transcription terminator sequence.

Protease inhibitors (PI's) are part of the defensive response of plants towards feeding insects (Ryan, 1990). They are produced in large quantities in wounded leaves, and reversibly bind to the insect digestive proteases (Jongsma & Boller, 1997). It appears that some insects have overcome this defense of their host plants. These insects have available a set of proteases which is insensitive to the inhibitors of the host plant. This set is induced when plant PIs are ingested, while other, presumably sensitive proteases are down-regulated (Jongsma et al., 1995a; Bown et al., 1997). To control such insect pests, it is the inventors' aim to complement the plant's arsenal with PIs that do inhibit these insensitive proteases. The strategy to generate these complementary inhibitors is by modifying existing plant inhibitors, using phage display to select variants that bind tightly to gut proteases (Jongsma et al., 1995b). Phage display is a powerful tool to adapt the specificity of protease inhibitors. Phage display of mammalian Kunitz domain inhibitors has proven a very efficient tool to select high affinity PIs (Roberts et al., 1992; Markland et al., 1996; Dennis & Lazarus, 1994).

A phase display system was started up, to adapt the specificity of the potato protease inhibitor 2 (PI2). This inhibitor is abundantly expressed in plants, and has been implicated in plant defense (Johnson et al., 1989). PI2 was isolated from potato tubers and tomato leaves as a double-domain inhibitor, and was reported to inhibit both trypsin and chymotrypsin (Bryant et al., 1976). The PI2 gene under study encodes a mature protein of 123 amino acids with two putative active site domains. The crystal structure of an inhibitor-proteinase complex reveals that a stretch of 10 amino-acids, corresponding to residues 57–60 of the second inhibitor domain interacts with a trypsin-like catalytic domain (Greenblatt et al., 1989).

In a previous study, it was reported that PI2, when displayed as a fusion with fd gene 3 (g3), is intact and functionally active (Jongsma et al., 1995b). Also it was shown that a PI2 variant with an intact trypsin binding site, when displayed on a phage, could be readily selected from a background of 10,000 inactive alanine mutants in three rounds of panning on bovine trypsin. As a next step, it was set out to select trypsin binding variants from a pool that had been randomized in the trypsin binding domain.

In the following, the invention is more precisely described by reference to FIGS. 1 to 4.

LEGENDS TO FIGURES

FIG. 1

DNA sequences of the active-site domains of wild-type PI2 (a) (Domain 1: SEQ ID NO:2 and Domain 2: SEQ ID NO:3) and the library of PI2-variants (b) (Domain 1: SEQ ID NO:4 and Domain 2: SEQ ID NO:5). For generation of the library of mutants, we amplified a 226 bp fragment using primers 32407 (5'GGGTGCGGCCGCTTCCATTGCAGGGTACATATT TGC3') SEQ ID NO:6 and 39972 (5'CCGACGGCATGCNNKNNKNNKTGCGATCCACA TATTGCC3') SEQ ID NO:7 from template pB302, digested the fragment with SphI and NotI enzymes, and ligated the resulting 207 bp, after gel-purification, into SphI-NotI digested and gel-purified large fragments of either pB304 (Jongsma et al., 1995b), pRlac304 or pRpsp204. Ligation mixtures were transformed to XL-1 blue and plated on LB-agar, supplied with 2% glucose, 20 ug/ml Tc (tetracycline) and 100 ug/ml Ap (ampicilline) in such dilutions that colonies did not merge. After overnight growth, about 10e5 colonies for each vector were resuspended in 15 ml LB, supplied with 15% glycerol, and stored at −80° C. To generate phage stocks cells were taken from −80° C. and plated in such dilutions that colonies did not merge. $10^5$ colonies were then resuspended in 15 ml LB, and bacterial suspension was subsequently diluted until the absorption at 600 nm was about 0.1, as compared to sterile LB. This dilution was grown and infected with helperphage VCSM13, and variant PI2-phages were grown, isolated and purified as described in Jongsma et al. (1995b). The pRpsp2-library was grown in 2×YT medium, and glucose was not added to the culture that was infected by helperphage, but was otherwise not treated differently from the other libraries. Three rounds of panning selections were performed with about $10^{12}$ phages carrying the pB3-vector as described in Jongsma et al. (1995b). Quickscreen selection (Markland et al., 1996) was performed with all three libraries. For quickscreen, bovine trypsin (Sigma) was biotinylated, purified on a PD-10 column (Pharmacia) and mixed with about $10^{12}$ phages in a concentration of 2 nM, in 1 ml phosphate buffer saline, containing 2% non-fat dry milk powder, and 0.2% tween 20 (PBSET). After incubating for 30 minutes at room temperature, 20 ul streptavidin coated paramagnetic beads suspension (Dynal) was added and incubated again for 30 minutes. Subsequently, beads were captured using a Dynal MPC magnet, washed 6 times with ice-cold PBSET, and incubated 30 minutes with 1 ml 0.1 N HCl-glycine pH=2.2 with 1% BSA, to elute the phages from the trypsin. The beads were captured and discarded, while the supernatant was neutralized with 60 ul 2M tris pH10 solution. The eluate of the first selection round was added to biotinylated trypsin, and the selection procedure was repeated two times. Phages from the last elution fraction were reinfected in XL-1 blue and plated on LB-agar, supplied with glucose, Tc and Ap.

FIG. 2:

(A) pB3 is described in Jongsma et al. (1995b), and was constructed from pCANTAR5 (Pharmacia), by replacing the 1271 bp NcoI-EcoRI fragment containing the M13 gene 3 fragment by the 1316 bp NcoI-EcoRI fragment from pHEN1 (Hoogenboom et al., 1991). (B) From this plasmid, the 1371 bp AflIII-ScaI fragment was replaced by the corresponding fragment of pBR322, resulting in pRlac3. (C) Plasmid pRpsp2 was made by amplifying the minimal psp promoter using pJARA112 (Rakonjac et al., 1997) as a template, and two primers: #55, 5' ccgGTTAACcatgalgaaattcgccac and #56, 5' ggaattcCATatgttgtcctcttgattt. The amplified fragment was then SEQ ID NO:9 cleaved with HpaI and NdeI and ligated to the large fragment of HpaI NdeI cleaved vector pET25b (Novagen). The obtained plasmid was called pJARA116, Plasmid pJARA116 was cleaved with NcoI and ScaI and the larger fragment (3194 bp) was ligated to the larger (~2700 bp) NcoI/ScaI fragment of pB3.

FIG. 3

(A) Density of XL-1 blue cultures harbouring plasmids pB3, pB3-PI2, pB3-D1 and pB3-F1 measured over 24 hours. Colonies were grown overnight at 37° C. on LB-agar medium containing 2% glucose, 20 ug/ml tetracyclin and 100 ug/ml ampicillin. A well-separated colony was transferred to 1 ml liquid LB medium with the same ingredients, and grown overnight at 37° C. while shaking at 300 rpm. An aliquot of 100 ul of the overnight culture was spun down, washed with LB medium, and resuspended in 10 ml LB, supplemented with 2% glucose and 100 ug/ml Ap. The density of the culture was measured as adsorption by 1 ml of culture at 600 nm in a Vitalab 10 (Vital Scientific, Dieren NL), relative to the absorption of 1 ml of sterile medium.

When the density of the culture rose above 0.3, 100 ul culture was diluted in 1 ml of LB, prior to measurements. The complete experiment was repeated three times. The displayed curves are from a single representative experiment. (B) Density of XL-1 blue cultures harbouring plasmids pRpsp2, pRpsp2-PI2 and pRpsp2-D1 measured over 24 hours. Growthcurves were determined as described in 3a.

FIG. 4

Western blot of serial dilutions of pRlac3-PI2 phages and pRpsp2-PI2 pages. Phage solutions were prepared as described in Jongsma et al. (1995b). Solutions were diluted serially in sample buffer, diluting threefold in every step. After electrophoresis on a 10% poly-acrylamide/SDS gel and electroblotting onto nitrocellulose, g3 protein and g3-PI2 fusion protein were detected by anti-g3 antiserum (Mobitec).

FIGS. 5A–5C

The DNA sequence of phagemid vector pRpsp2 SEQ ID NO:1.

The features and positions are the following:

| feature | product | position |
| --- | --- | --- |
| bla | beta lactamase | 201–1039 |
| ori | pBR322 origin of replication | 1724 |
| rop | Rop | 2432–2244 |
| Ppsp | psp promoter | 3479–3647 |
| pelB | signal peptide pelB | 3647–3710 |
| mcs | multiple cloning site | 3711–3754 |
| myc | c-myc tag | 3755–3804 |
| amber | amber stopcodon | 3806–3807 |
| gIII | fd gene 3 | 3808–5021 |
| ori-fd | fd origin of replication | 5407 |

EXPERIMENTAL AND DISCUSSION

A library of PI2 variants does not yield active variants

In a preliminary experiment, it was tried to select inhibitors of bovine trypsin from a small pool of PI2 variants. This pool was constructed in vector pB3, a derivative of pHEN1 and pCANTAB5 (Hoogenboom et al., 1991; Jongsma et al., 1995; FIG. 2A). Variation was directed to inhibitor domain II (codons 61–63) of the PI2-gIII fusion gene, while domain I (codons 4–6) was inactivated by replacing its three central residues with alanines. Codons for the three central residues of domain II (PRN) were replaced by NNK triplets (N=A, T,C,G; K=T,G). This was presumed to give rise to 32,000 different variants on the DNA level. With this pool, three rounds of selection were performed on bovine trypsin.

Sequence analysis of selected clones revealed that five out of nine phages encoded no fusion protein at all, as a result of deletions of large regions including the PI2 sequence. The other four clones carried variants of the fusion protein with amber stopcodons within the variegated part (table I), in addition to the stopcodon at the fusion of PI2 and g3 (Jongsma et al., 1995). Amber stopcodons (TAG) are suppressed by the supE mutation in XL-blue, with an efficiency ranging from 0.7% to 25%, depending on the nature of the codon following the TAG (Miller & Albertini, 1983). The codons that follow the TAG's in the selected PI2-amber variants consistently allow 2% to 3% suppression. This means that the level of full-length fusion protein synthesized by these mutants is much reduced. Apparently, the procedure selects against phages that encode intact g3p fusions.

Not finding any variants that resemble the wild-type PI2 came as a surprise. The mutant PI2[Ala$^{4-6}$,PRN$^{61-63}$] has a Ki for trypsin of 0.4 nM and was expected to be represented in the library of 8000 variants. However, the same selection protocol, which was capable of retrieving a single PI2 [Ala$^{4-5}$,PRN$^{61-63}_{4-6, 61-63}$] phage from a background of 10,000 PI2[ALA$^{4-6}$] phages (Jongsma et al., 1995), could not do the same with the PI2 library. Rather, it favoured incomplete variants.

TABLE I

Partial deduced amino-acid sequences and binding properties of phages that bind trypsin

| vector | sequence | ELISA$^a$ | P2 residue | K$_1$ (nM)$^d$ |
| --- | --- | --- | --- | --- |
| pB3 | PRN | 100% | hydrophobic | 0.4 |
|  | AAA | 31% | hydrophobic | 400 |
|  | LV#$^b$ | 28% | hydrophobic |  |
|  | SI# | nd | polar |  |
|  | #RS | 34% | polar |  |
|  | #RH | 63% | polar |  |
|  | 5 deletions$^c$ | 15% | — |  |
| pRlac3 | PRN | 100% | hydrophobic |  |
|  | AAA | 16% | hydrophobic |  |
|  | LRH | 87% | hydrophobic |  |
|  | VRH | 72% | hydrophobic |  |
|  | YRS | 70% | polar |  |
|  | FRS | 66% | hydrophobic |  |
|  | VR3 | 65% | hydrophobic | 0.8 |
|  | VRS | nd | hydrophobic | 0.8 |
|  | HRS | 50% | polar | 0.4 |
|  | HR3 | nd | polar | 0.4 |
|  | FRA | nd | hydrophobic |  |
|  | PLG | 17% | hydrophobic |  |
|  | ASC | 5% | hydrophobic |  |
| μRpsp2 | PRN | 100% | hydrophobic |  |
|  | AAA | 30% | hydrophobic |  |
|  | SRH | 192% | polar | 0.3 |
|  | KRS | 187% | charged | 0.5 |
|  | KR3 | nd | charged | 0.5 |
|  | RRS | 185% | charged | 0.15 |
|  | RRS | nd | charged | 0.15 |
|  | QRS | 160% | polar |  |
|  | IRQ | 140% | hydrophobic |  |
|  | NRQ | 107% | polar |  |
|  | TRS | 15% | polar |  |
|  | ARS | nd | hydrophobic |  |
|  | EYF | 12% | charged |  |
|  | #VF | nd | polar |  | legend to table I
$^a$Comparable numbers of phage particles were analyzed in a phage ELISA, as described in Jongsma et al., 1995. ELISA signals at 405 nm did not exceed 1.0 units. For every vector the signal generated by the PRN mutant was taken as the 100% value, to which the other signals were compared. The uncorrected ELISA signal of the pRpsp2-vector phages was much lower than that of the pRlac3 phages (not shown). This is in agreement with the lower display level of the psp-promoter, as described above.
$^b$Hatches indicate a TAG-stopoodon, recognized by the supE suppressor as Cln codon.
$^c$Deletions were observed as plasmids that could not be sequenced with a primer complementary to c-myc-tag, at the fusion of the PI2 gene and g3 (Jongsma et al., 1995b), and appeared as plasmids with considerably increased mobility in a 0.7% agarose gel (not shown).
$^d$Trypsin (final concentration = 15 nM) was allowed to associate with increasing amounts of inhibitor for 30 minutes in 130 ul of 10 mM CaCl$_2$, 100 mM Tris-HCl (pH = 8). The assay was initiated by the addition of 50 ul BApNA (Sigma) (final concentration = 1 mM). The increase of the absorption at 405 nm was followed during 30 minutes. Data were interpreted according to Green and Work (1953).

A selection disadvantage for fusion-protein encoding plasmids

Figure 3A:
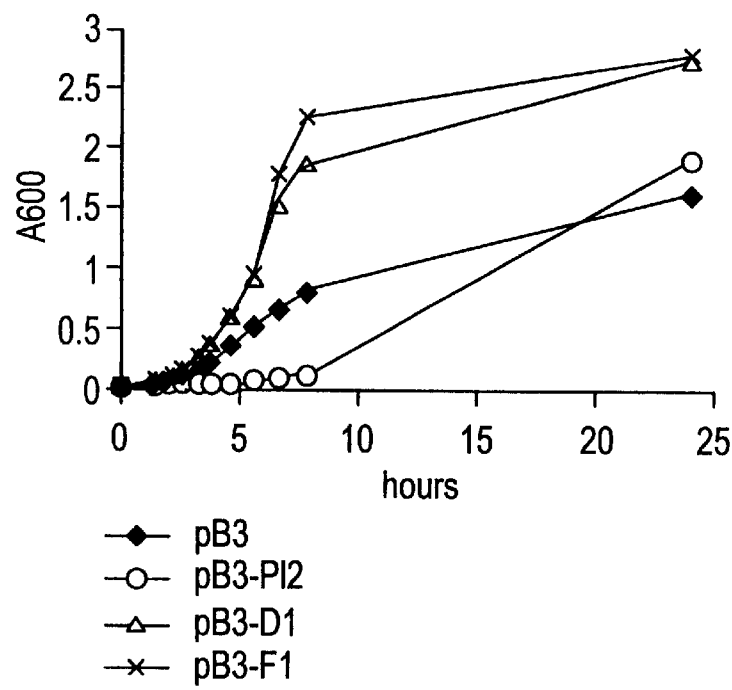
Figure 3B:
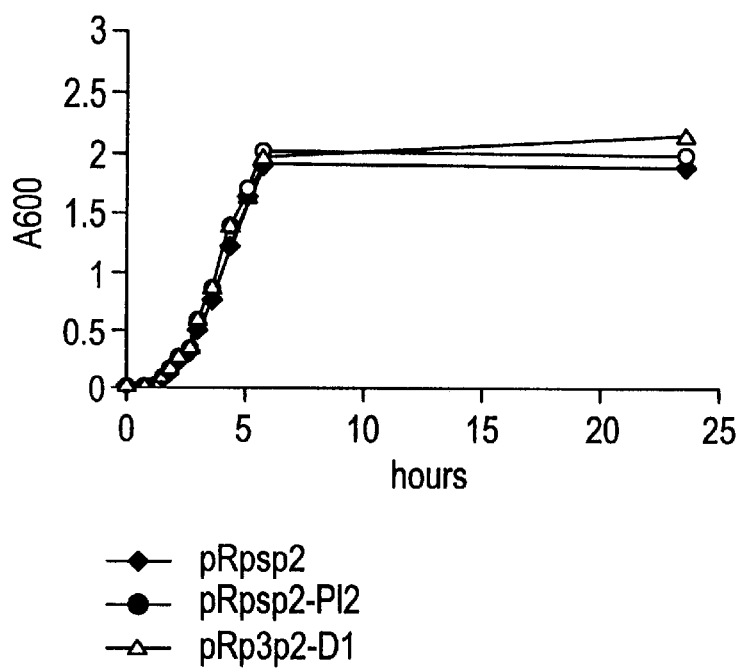

An explanation for the selection of deletion and amber variants could be that these may have a considerable growth advantage over variants that carry the intact PI2-g3 fusion gene. To test this, the growth of E. coli cells carrying plasmids pB3 (encoding g3) and pB3-PI2 (encoding PI2-g3 fusions; Jongsma et al., 1995b) was compared to an amber mutant (pB3-D1) and a deletion mutant (pB3-F1), that were isolated after selection rounds on trypsin (FIG. 3A). In spite of the presence of 2% glucose in the growth medium to suppress the lac-promoter, there is a clear difference between plasmids that encode g3 and plasmids that do not. The pB3 plasmid, encoding the g3 protein, confers slower growth than variants with an amber stopcodon in domain II, or deletion variants. The PI2-g3 fusion of pB3-PI2 allows only very poor growth.

Construction of new phagemid vectors

As a comparison a phagemid was made in which the copynumber of the pB3 vector was lowered. As argued by De Boer et al. (1983), fewer copies per cell of the plasmid would provide a better balance between lac-promoter DNA and lacl-repressor protein. A phagemid vector, pRlac3, was constructed which carries the low-copynumber origin of replication of pBR322 (FIG. 2B). This modification was expected to reduce the copynumber to about 30 per cell, instead of 500 as in the case of pUC-derived vectors like pB3 (Sambrook et al., 1989).

A phagemid of the invention was constructed by replacing the lac-promoter by the promoter of the *E. coli* phage-shock-protein (Psp) operon. The psp-promoter is repressed under normal growth conditions, and induced by filamentous phage infection. The mechanism of induction of this promoter is discussed by Model et al. (1997). It was found by the inventors that a plasmid which carries g3 under control of the psp-promoter could complement a g3-deleted helperphage (Rakonjac et al., 1997). This observation suggests that the basal level of transcription is quite low, but the extent of induction of this promoter is satisfactory for phage display of g3 fusion products. Therefore experiments were initiated to assess the virtues of the psp-promoter for phage display of PI2.

Phagemid vector pRpsp2 (FIG. 2C) was constructed, in which g3 is controlled by the psp-promoter. Instead of its native leader, g3 is fused to the signal sequence of the pelB gene. As an additional feature, plasmid pRpsp2 includes the rop gene from pBR322, which reduces the copynumber an additional twofold, relative to the pRlac3 vector (Cesareni et al., 1982). The DNA sequence of plasmid pRpsp2 is shown in FIG. 5.

New vectors reduce the disadvantage of intact fusion genes

The effect on bacterial growth of the PI2 gene in the context of the new vectors was studied. The wild-type PI2-g3 and amber PI2-g3 genes were recloned in low-copynumber variant pRlac3 and psp-promoter variant pRpsp2, which resulted in clones pRlac3-PI2, pRlac3-D1, pRpsp2-PI2, and pRpsp2-D1. Growth rates of bacteria harboring these phagemids were again compared. The wild-type and amber construction in both pRlac3 and pRpsp2 (FIG. 3B) differed very little, if at all, in growth rate. For pRlac3-PI2, some variation in growth rate between individual clones with the same genotype was observed. This was also reflected in a variable size of the colonies on an agar plate containing glucose. Colonies of pRpsp2 constructs were all equal.

As it appears, growth-biases due to toxicity of the inserts are reduced in the new vectors. The changes that were made in the vectors to achieve this may have affected several figures that are relevant to phage display. Therefore, some additional experiments were done.

Display level of low-copy number and psp vectors

Figure 4:
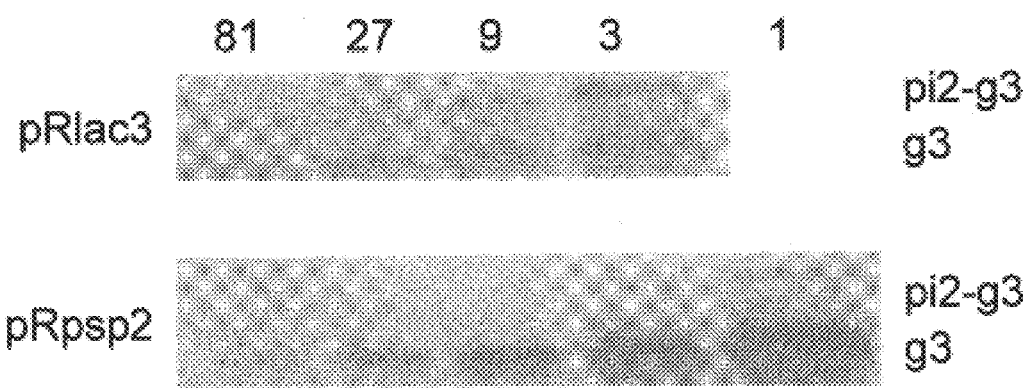

A possible disadvantage of the new vectors, as compared to the old system, could be that tightly-controlled expression of fusion-protein in the bacterium might result in a lower number of copies on the surface of the phage particles. The display level of each of the vectors was determined on the basis of the ratio of fusion protein to native g3 protein in phage particles. The three vectors (FIG. 2) harboring the intact PI2 gene were compared. Phage particles were obtained by rescue with helperphage VCSM13, and their concentration normalized, as judged by their DNA content (Rakonjac et al., 1997). Subsequently, a series of dilutions of phage samples were blotted and the g3 p and PI2-g3 proteins were detected by a monoclonal anti-g3p antibody. The dilution factor was determined at which either the g3-PI2 fusion protein, or the wild type g3 protein, could no longer be detected by visual inspection (FIG. 4). The ratio of these dilution factors was used as a measure for display level. The observed levels of display for the various constructs appear to be dependent on the promoter used, and not on other parameters, such as plasmid copynumber or bacterial growthrate. For constructs using the lac-promoter, pB3-PI2 and pRlac3-PI2, it is estimated that 10% of g3 protein consists of fusion protein. This is comparable to what is reported for other systems (Cwirla et al., 1990; Röttgen & Collins, 1995). In case of the psp promoter construct, pRpsp2-PI2, the level of display is reduced to approximately 2.5%. Phagemid vectors without rop-gene, but carrying the psp-promoter, promote a similar display level. This indicates that the reduced display level of pRpsp2 is due to the psp-promoter, and not to the plasmid copy number.

If the fusion proteins are incorporated into particles according to a normal distribution, and five g3 proteins per particle are assumed, these frequencies means that the lac-promoter allows roughly 33% of the particles to carry one inhibitor, compared to 9% of the psp promoter phages. The number of polyvalent phages is calculated to be 8% in case of the lac-promoter constructs, and only 0.4% for the psp-promoter constructs. As a result, the relative number of polyvalent phages as compared to monovalent phages is reduced about five-fold in the psp-vectors. This would mean that the use of the psp-vector favors selection for affinity, rather than avidity.

Copynumber does not affect the phagemid packaging efficiency

A disadvantage of low-copynumber phagemids could be that their DNA is packaged with a lower efficiency, relative to the helper-phage DNA. This would result in a relatively high fraction of particles that do display the fusion protein, but do not carry its gene. The packaging efficiency of phagemid DNA versus helperphage DNA was determined (table II). After infecting cultures of vector constructs pB3, pRlac3 and pRpsp2 with VC3M13 helperphage, cells were grown overnight. The number of particles carrying phagemid DNA and helperphage DNA was compared. Surprisingly, it was observed that both new vectors show an improved packaging efficiency of the phagemid DNA relative to helperphage DNA.

TABLE II

Packaging efficiency of plasmid DNA and helperphage DNA

| | pB3 | pRlac3 | pRpsp2 |
|---|---|---|---|
| phagemid (cfu)[a] | 2.88e12 | 2.46e12 | 1.41e12 |
| helperphage (pfu) | 6e10 | 4e10 | 9.4e9 |
| ratio phagemid/phage | 48 | 61 | 150 |

TABLE II-continued

Packaging efficiency of plasmid DNA and helperphage DNA

|  | pB3 | pRlac3 | pRpsp2 |
|---|---|---|---|

[a]The number of particled containing phagemid DNA or phage DNA was determined as follows: XL-1blue cells harboring one of the plasmids (pB3 pRlac3 or pRpsp2) were grown to $A_{600} = 0.4$ in 2xYT medium, supplied with 60 ug/ml Ap and 2% glucose. Cells were infected by VCSM13 helperphage (m.o.i = 50) during 1 hour, after which cells were pelleted to remove free phages. Cells were resuspended in 2xYl medium (supplied with 50 ug/ml Ap and 30 ug/ml Km) and grown overnight at 30° C. while shaking at 300 rpm. Cells were removed by ocntrifugation, and supernatants were incubated at 65° C. for 10 minutes to remove residual bacteria. The supernatant was serially diluted, mixed (on ice) with fresh and chilled exponentially growing culture of XL-1 blue cells, incubated on ice for 1 hr, and aliquots were plated on LR-agar with 2% glucose supplied with 60 ug/ml Ap to count colony forming units, or in a top lawn with 2% glucose to count plaque forming units.

Resistance to helperphage infection

Expression of g3 protein from a plasmid renders the cell inaccessible to phage infection (Bocke et al., 1982). In a phage-display system using phagemids and helperphage, this means that tight control of fusion-protein synthesis is needed, since poorly controlled cells that express g3p cannot be infected by helperphage, and will not produce phages. The pRlac3 and pRp3p2 plagemids were constructed to improve this control, and can thus be expected to allow more efficient helperphage infection. The new vectors were compared to pB3, by testing the fraction of ampicillin-resistant cells that can accept helper infection during one hour of infection. Results are shown in table III.

Infection by helperphage of either pB3 or pRlac3 containing cells is always lower than 100%. Since variation between experiments is large, it is difficult to conclude that copynumber has an effect on superinfection. In contrast, phagemid pRpsp2 reproducibly permits 100% helperphage infection. Constructs with the psp-promoter, but lacking the rop-sequence, did not show this effect. Apparently, the improved repression of gene III seems to result from a favorable context for the psp-promoter, caused by the presence of additional pBR322 sequences upstream of the promoter region.

TABLE III

Bacteria harboring different vectors, superinfected by VCSM13 helperphage.

| vector | % infected bacteria[a] |
|---|---|
| pB3 | 75 ± 20 |
| pR3 | 72 ± 24 |
| pRpsp2 | 90 ± 1 |

[a]Cells in the exponential phase of growth in 2xYT medium that contained Ap (60 ug/ml) were infected with helperphage VC3M13 at m.o.i. = 50. One hour later, the number of infected cells is assayed by plating dilutions of the infected cultures on LB agar, supplied with Ap (60 ug/ml) and Km (30 ug/ml). This number is compared to the total number of cells calculated from the number of colonies on plates supplied with only ampicillin (60 ug/ml). Host strain was XL-1 blue. Bacteria that carried pB3 and pR3 were propagated and plated in the presence of 2% glucose.

Selection of trypsin binding phages with new vectors

The above described experiments suggest that vectors pRlac3 and particularly pRpsp2 are to be preferred over the original pB3 vector. To confirm this, libraries of 8000 variants of potato inhibitor PI2, similar to the one available in pB3, were constructed in pRlac3 and pRpєp2 (FIGS. 1 and 2). These libraries were all subjected to selection on trypsin, as described above for the pB3 library, and sequence analysis of a number of selected phagemids was performed.

Sequence analysis of 11 (pRlac3) and 12 (pRpsp2) clones selected from each of the two new libraries reveals two major features: firstly, none of the phages with the new vectors have deletions (Table I) which is in marked contrast with the selected clones in the original vector. Only one amber mutant is observed in the psp-population. Instead of deletion and amber-variants, 9 out of 11 (pRlac3) and 10 out of 12 (pRpsp2) selectants encode a PI2 variant which fits the consensus XRX. Trypsin is known to preferentially bind substrates or inhibitors with arginine as the central (P1) residue (Polgar, 1989). Therefore, the XRX consensus strongly suggests that these phages have been selected for their ability to bind trypsin, and not for all their reproductive advantages. In addition, six out of nine phages (7 out of 10 or pRpsp2) fit the consensus XRS. The first (P2) position shows a less clear preference. Here, phage display with the two new vectors results in different types of residues. Hydrophobic amino-acids are dominant at the P2 position of the pRlac3 selectants (eight out of eleven), and charged residues are absent. In contrast, five out of twelve selected clones with pRpsp2 carry a positively charged residues (lysin, arginin) in the P2 position.

The consensus sequence XRX of the selected phage clones suggested that these bind trypsin. To assess the binding of the phages, clonal phage samples were generated for a number of selectants, and analyzed by phase ELISA. The phage ELISA signal roughly corresponds to the affinity of the encoded inhibitor for the target enzyme (B. Schipper & M. Jongsma, unpublished results). ELISA signals were compared to that of a negative- and positive-control PI2 variant, cloned in the corresponding vector. The mutants PI2[$Ala^{4-8, 61-63}$] and PI2 [$Ala^{4-6}$; $PRN^{61-83}$], were used for this purpose, respectively. The ELISA signals relative to the positive control PI2 are depicted in table I (second column).

As compared to the control phages, the pRpsp2-phages generally show better binding than the positive control, while the pRlac3 phages have somewhat lower binding, which can however be clearly distinguished from the negative control. It is concluded that both vectors lead to the selection of trypsin binding phages, which contrasts to our findings with the more cannonical pB3 vector.

The affinity of selected protease inhibitors is sub-nanomolar

Unfortunately, PI2 is not produced in sufficient quantities in the periplasmic space to allow an easy analysis of the affinity of selected variants as soluble proteins. Therefore expression in yeast was carried out. Out of the selected PI genes of both the pRlac3 and pRpsp2 libraries, three variants from each library were chosen. Variants LRH and SRH were chosen for giving the highest ELISA signal in the phage binding tests (Section 2.8; table I, second column), Variants VRS, HRS, KRS and RRS all appeared two times in the pool of selected variants that were analyzed. These PI2 variants were transferred to vector pPIC 9 (Invitrogen) and transformed to *Pichla pastoris* (Cregg et al., 1993). After growing yeasts cultures, inhibitors were purified from the medium by FPLC on a High Trap SP column (Pharmacia Biotech.) and the inhibitory activity towards bovine trypsin measured by the method of Green & Work (1963). The LRH variant could not be produced in yeast.

The determined $K_i$ values are in the fourth column of table I. These observations can be made: (1) The affinity for trypsin of the PI's selected by phage display is in the same range as that of the wild-type PRN variant (K=0.4 nM), while the $K_i$ of the AAA mutant is thousand-fold worse. (2) There is no major difference in the affinities of the PI's selected from libraries in vector pRlac3 or pRpsp2, although the best variants characterized here ($K_i$=0.15 nM) have been isolated using pRpsp2, (3) The differences in the phage ELISA signals do not correlate with the measures $K_1$ values. Probably, this observation reflects differences in display level of individual clones.

Notably, charged residues are absent in the pRlac3 variants, but well-represented in the pRpsp2 variants. Although this does not result in dramatically different $K_1$ values, it strongly suggests that the pRlac3 library is biased to non-charged P2 residues, and the pRpsp2 vector is not.

The finding that with the pRpsp2 vector, different amino acid residues were selected at the P2 position as compared to the pRlac3 vector is relevant. It demonstrates that with the availability of the pRpsp2 vectors, a broader spectrum of amino acid sequences can be sampled. This implies that molecules can be selected from a more diverse pool of variants resulting in a higher probability of selecting desired variants.

References

Boeke, J., Model, P., Zinder, N. D., 1982, Effects of bacteriophage f1 gene III protein on the host cell membrane, Mol. Gen. Genet. 186, 185–192.

Bown, D. P., Wilkinson, H. S., Gatehouse, J. A., 1997, Differentially regulated inhibitor-sensitive and insensitive protease genes from the phytophagous insect pest, Helicoverpa armigara, are members of complex multigene families. Insect Biochem. Mol. Biol. 27, 625–638.

Bradbury, A., 1998, Diversity by design. Trends in Biotech. 16, 99–102.

Bryant, J., Green, T. B., Gurusaddalah, I., Ryan, C. A., 1976, Proteinase inhibitor II from potatoes: Isolation and characterization of its promoter components. Biochemistry 15, 3418–3424.

Cesareni, G., Muesing, M. A., Polisky, B., 1982. Control of ColE1 DNA replication: The rop gene product negatively affects transcription from the replication primer promoter. Proc. Natl. Acad. Sci. USA 79, 6313–6318.

Cregg, J. M., Vedvick, T. S., Raschke, W. C., 1993, Recent advances in the expression of foreign genes in *Pichia pastoris*. Bio/Technology 11, 905–910.

Cwirla, S. E., Peters, E. A., Barrett, R. W., Dower, W. J., 1990. Peptides on phage: A vast library of peptides for identifying peptides. Proc. Natl. Acad. Sci. USA 87, 6378–6382.

de Boer, H. A., Cornstock, L. J., Vasser, M., 1983: The tac promoter: A functional hybrid derived from the trp and lac promoters. Proc. Natl. Acad. Sci. USA. 80, 21–25.

Dennis, M. S., Lazarus, R. A., 1994. Kunitz domain inhibitors of tissue factor-factor VIIa. I. Potent inhibitors selected from libraries by phage display. J. Biol. Chem. 269, 22129–22136.

Duenas et al., 1994. Clonal selection and amplification of phage displayed antibodies by linking antigen recognition and phage replication. Bio/Technology 12, 999–1002.

Duenas, M., Malmborg, A. C. Casalvilla, R., Ohlin, M., Borrebaeck, C. A., 1996, Selection of phage displayed antibodies based on kinetic constants. Mol. Immunol. 33, 279–95.

Gramatikoff et al., 1995. Direct interaction rescue, a novel filamentous phage technique to study protein-protein interactions. Nucleic Acids Research 22, 5761–5762.

Green, N. M., Work E., 1953. Pancreatic trypsin inhibitor 2. Reaction with trypsin. Biochem. J. 54, 347–352.

Greenblat, H. M., Ryan, C. A., James, M. N. G., 1989, Structure of the complex of Streptomyces griseus proteinase B and polypeptide chymotrypsin inhibitor-1 from Russel Burbank potato tubers at 2.1 A resolution. J. Mol. Biol. 205, 201–228.

Hoogenboom, H. R., Griffiths, A. D., Johnson, K. S., Chiswell, D. J., Hudson, P., Winter, G., 1991, Multi-subunit proteins on the surface of filamentous phage: Methodologies for displaying antibody (Fab) heavy and light chains. Nucleic Acids Res. 19, 4133–4137.

Jespers et al. (1995). Surface expression and ligand based selection of cDNAs fused to filamentous phage gene VI, Bio/Technology 13, 378–382.

Johnson, R., Narvaez, J., An, G., Ryan, C. A., 1989, Expression of proteinase inhibitors I and II in transgenic tobacco plants: Effect on natural defense against Manducas sexta larvae, Proc. Natl. Acad. Sci. USA, 86, 9871–9875.

Jongsma, M. A., Bakker, P. L., Peters, J., Bosche, D., Stiekema, W. J., 1995a, Adaptation of Spodoptera exigue larvae to plant proteinase inhibitors by induction of proteinase activity insensitive of inhibition. Proc. Natl. Acad. Sci. USA. 92, 8041–8045.

Jongsma, M. A., Bakker P. L., Stickema, W. J., Bosch, D., 1995b. Phage display of a double-headed proteinase inhibitor: analysis of the binding domains of potato proteinase inhibitor II, Molecular Breeding 1, 181–191.

Jongsma, M. A., Bolter, C., 1997. The adaptation of insects to plant protease inhibitors, J. Insect. Physiol. 43, 885–895.

Knappik, A., Pluckthun, A., 1995, Engineered turns of a recombinant antibody improve its in vivo folding. Protein Eng. 8, 81–89.

Krebber et al., 1995. Co-selection of cognate antibody-antigen pair by selectively infective phages. FEBS Letters 377, 227–231.

Krebber, A., Burmeister, J., Pluckthon, A., 1996, Inclusion of an upstream transcriptional terminator in phage display vectors abolishes background expression of toxic fusions will coat protein g3p. Gene 178, 71–74.

Maenaka, K. Furuta M., Tsumoto, K., Watanabe, K., Ueda, Y., Kumagai, I., 1996; A stable phage-display system using a phagemid vector, phage display of hen egg-white lysozyme (HEL), *Escherichia coli* alkaline, phosphatase, and anti-HEL monoclonal antibody, HyHEL10. Biochem Biophys. Res. Comm. 218, 682–687.

Markland, W., Ley, A. C., Lee, S. W., Ladner, R. C., 1996. Iterative optimization of high-affinity proteases inhibitors using phase display. 1. Plasmin. Biochemistry 35, 8045–8057.

Miller et al. (1983), Effects of surrounding sequence on the suppression of nonsense codons. J. Mol. Biol. 164, 59–71.

Model, P. Jovanovic, G., Dworkin, J., 1997. The *Escherichia coli* phage shock-protein (psp) operon, Mol. Microbiol. 24, 255–261.

Morett et al., 1993. The sigma 54 bacterial enhancer binding protein family: mechanism of action and phylogenetic relationship of their functional domains. J. Bacteriology 175, 6067–6074.

Polgar, L., 1989, Mechanisms of protease action. CRC Press Inc., Boca Raton, Fla.

Rakonjac, J., Jovanovic, G., Model, P. 1997. Filamentous phage infection-mediated gene expression: construction and propagation of the gII deletion mutant helper phage R408d3. Gene 198, 99–103.

Roberts, B. L., Markland, W., Ley, A. C., Kent R. B., White D. W., Guterman S. K., Ladner, R. C., 1992. Directed evaluation of a protein: selection of potent neutrophil elastase inhibitors displayed on M13 fusion phage. Proc. Natl. Acad. Sci. USA. 89, 2429–2433.

Röttgen, P., Collins, J., 1995. A human pancreatic secretory trypsin inhibitor presenting a hypervariable high constrained epitope via monovalent phagemid display. Gene 164, 243–250.

Ryan, C. A., 1990, Protease inhibitors in plants: Genes for improving defenses against insects and pathogens. Ann. Rev. Phytophath. 28, 425–449.

Sambrook, J., Fritsch, E. F., Maniatis, T., 1989, Molecular cloning. A laboratory manual, second ed. Cold Spring Harbor Laboratory Press, Cold Spring Harbor.

Smiley, J. A., Benkovic, S. J., 1994, Selection of catalytic antibodies for a biosynthetic reaction from a combinatorial cDNA library by complementation of an auxotrophic *Escherichia coli*: antibiotics for orotate decarboxylation. Proc. Natl. Acad. Sci. USA, 91, 8319–8323.

Tan, S., Conoway, R. C., Weliky-Conoway, J., 1994, Rapid simultaneous screening for DNA integrity and antigen specificity of clones selected by phage display. BioTechniques 16, 826 830.

What is claimed is:

1. A collection of phagemids comprising:
   i) a promoter operatively linked to a gene coding for a translational fusion between a peptide and a filamentous single strand DNA bacteriophage coat protein or a part thereof, which promoter is the promoter of the *E. coli* phage-shock-protein (psp) operon, which promoter is induced by expression of gene IV of a filamentous bacteriophage,
   ii) a replication origin derived from a filamentous single strand DNA bacteriophage, and
   iii) a plasmid replication origin.

2. A collection of phagemids according to claim 1, characterized in that the plasmid replication origin is a low-copynumber origin of replication.

3. A collection of phagemids according to claim 2, characterized in that they further comprise the rop gene of pBR322.

4. A collection of phagemids according to claim 2, characterized in that they comprise in a 5' to 3' direction:
   the plasmid replication origin and the promoter operatively linked to the fusion gene.

5. A collection of phagemids according to claim 3, characterized in that they comprise in a 5' to 3' direction:
   the plasmid replication origin and the promoter operatively linked to the fusion gene.

6. A collection of phagemids according to claim 2, characterized in that the peptide is a variant of a protease inhibitor.

7. A collection of *E. coli* clones or cells representing a collection of phagemids according to claim 2, wherein the phagemids are carried in plasmid form.

8. A collection of phagemids according to claim 1, characterized in that they comprise in a 5' to 3' direction:
   the plasmid replication origin and the promoter operatively linked to the fusion gene.

9. A collection of phagemids according to claim 8, characterized in that the plasmid replication origin is the low-copynumber origin of replication of pBR322.

10. A collection of phagemids according to claim 8, characterized in that they further comprise the rop gene of pBR322 inserted between the plasmid replication origin and the promoter operatively linked to the fusion gene.

11. A collection of phagemids according to claim 8, characterized in that the promoter is operatively linked to the leader sequence of the pelB gene of Erwinia carotovora and the fusion gene.

12. A collection of phagemids according to claim 1, characterized in that the peptide is a variant of a protease inhibitor.

13. A collection of phagemids according to claim 12, characterized in that the peptide is a variant of potato protease inhibitor 2 (PI2).

14. A collection of *E. coli* clones or cells representing a collection of phagemids according to claim 1, wherein the phagemids are carried in plasmid form.

15. A collection of phagemids according to claim 1, characterized in that the plasmid replication origin is a low-copynumber origin of replication.

16. A collection of phagemids according to claim 1, characterized in that they comprise in a 5' to 3' direction:
   the plasmid replication origin and the promoter operatively linked to the fusion gene.

17. A collection of phagemids according to claim 1, characterized in that they comprise in a 5' to 3' direction:
   the plasmid replication origin and the promoter operatively linked to the fusion gene.

18. A collection of phagemids according to claim 1, characterized in that the peptide is a variant of a protease inhibitor.

19. A collection of *E. coli* clones or cells representing a collection of phagemids according to claim 1, wherein the phagemids are carried in plasmid form.

* * * * *

SEQUENCE LISTING

<160> NUMBER OF SEQ ID NOS: 9

<210> SEQ ID NO 1
<211> LENGTH: 5901
<212> TYPE: DNA
<213> ORGANISM: Escherichia coli

<400> SEQUENCE: 1

```
gacgaaaggg cctcgtgata cgcctatttt tataggttaa tgtcatgata ataatggttt      60
cttagacgtc aggtggcact tttcgggaa  atgtgcgcgg aaccctatt  tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gtttttgctc acccagaaac gctggtgaaa gtaaaagatg     300
ctgaagatca gttgggtgct cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgcagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
tcctttttga taatctcatg accaaaatcc cttaacgtga gttttcgttc cactgagcgt    1200
cagacccccgt agaaaagatc aaaggatctt cttgagatcc ttttttctg  cgcgtaatct    1260
gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg tcgggctga  acggggggtt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
```

-continued

```
gcagggtcgg aacaggagag cgcacgaggg agcttccagg gggaaacgcc tggtatcttt      1740
atagtcctgt cgggtttcgc cacctctgac ttgagcgtcg attttttgtga tgctcgtcag     1800
gggggcggag cctatggaaa aacgccagca acgcggcctt tttacggttc ctggcctttt      1860
gctggccttt tgctcacatg ttctttcctg cgttatcccc tgattctgtg ataaccgta       1920
ttaccgcctt tgagtgagct gataccgctc gccgcagccg aacgaccgag cgcagcgagt      1980
cagtgagcga ggaagcggaa gagcgcctga tgcggtattt tctccttacg catctgtgcg     2040
gtatttcaca ccgcatatat ggtgcactct cagtacaatc tgctctgatg ccgcatagtt      2100
aagccagtat acactccgct atcgctacgt gactgggtca tggctgcgcc ccgacacccg      2160
ccaacacccg ctgacgcgcc ctgacgggct tgtctgctcc cggcatccgc ttacagacaa     2220
gctgtgaccg tctccgggag ctgcatgtgt cagaggtttt caccgtcatc accgaaacgc      2280
gcgaggcagc tgcggtaaag ctcatcagcg tggtcgtgaa gcgattcaca gatgtctgcc     2340
tgttcatccg cgtccagctc gttgagtttc tccagaagcg ttaatgtctg gcttctgata      2400
aagcgggcca tgttaagggc ggttttttcc tgtttggtca ctgatgcctc cgtgtaaggg     2460
ggatttctgt tcatgggggt aatgataccg atgaaacgag agaggatgct cacgatacgg      2520
gttactgatg atgaacatgc ccggttactg gaacgttgtg agggtaaaca actggcggta     2580
tggatgcggc gggaccagag aaaaatcact cagggtcaat gccagcgctt cgttaataca      2640
gatgtaggtg ttccacaggg tagccagcag catcctgcga tgcagatccg gaacataatg     2700
gtgcagggcg ctgacttccg cgtttccaga ctttacgaaa cacggaaacc gaagaccatt      2760
catgttgttg ctcaggtcgc agacgttttg cagcagcagt cgcttcacgt tcgctcgcgt     2820
atcggtgatt cattctgcta accagtaagg caaccccgcc agcctagccg ggtcctcaac      2880
gacaggagca cgatcatgcg cacccgtggg gccgccatgc cggcgataat ggcctgcttc     2940
tcgccgaaac gtttggtggc gggaccagtg acgaaggctt gagcgagggc gtgcaagatt     3000
ccgaataccg caagcgacag gccgatcatc gtcgcgctcc agcgaaagcg gtcctcgccg     3060
aaaatgaccc agagcgctgc cggcacctgt cctacgagtt gcatgataaa gaagacagtc     3120
ataagtgcgg cgacgatagt catgccccgc gcccaccgga aggagctgac tgggttgaag     3180
gctctcaagg gcatcggtcg agatcccggt gcctaatgag tgagctaact tacattaatt     3240
gcgttgcgct cactgcccgc tttccagtcg ggaaacctgt cgtgccagct gcattaatga     3300
atcggccaac gcgcggggag aggcggtttg cgtattgggc gccagggtgg ttttctttt      3360
caccagtgag acgggcaaca gctgattgcc cttcaccgcc tggccctgag agagttgcag     3420
caagcggtcc acgctggttt gccccagcag gcgaaaatcc tgtttgatgg tggttaacca     3480
tgatgaaatt cgccacttgt tagtgtaatt cgctaactca tcctggcatg ttgctgttga     3540
ttcttcaatc agatctttat aaatcaaaaa gataaaaaat tggcacgcaa attgtattaa      3600
cagttcagca ggacaatcct gaacgcagaa atcaagagga caacatatga aatacctgct     3660
gccgaccgct gctgctggtc tgctgctcct cgctgcccag ccggcgatgg ccatggccca      3720
ggtgcagctg caggtcgacc tcgagatcaa acgggcggcc gcagaacaaa aactcatctc     3780
agaagaggat ctgaatgggg ccgcatagac tgttgaaagt tgtttagcaa aacctcatac      3840
agaaaattca tttactaacg tctggaaaga cgacaaaact ttagatcgtt acgctaacta     3900
tgagggctgt ctgtggaatg ctacaggcgt tgtggtttgt actggtgacg aaactcagtg     3960
ttacggtaca tgggttccta ttgggcttgc tatccctgaa aatgagggtg gtggctctga     4020
gggtggcggt tctgagggtg gcggttctga gggtggcggt actaaacctc ctgagtacgg     4080
```

-continued

```
tgatacacct attccgggct atacttatat caaccctctc gacggcactt atccgcctgg      4140
tactgagcaa aacccgcta atcctaatcc ttctcttgag gagtctcagc ctcttaatac       4200
tttcatgttt cagaataata ggttccgaaa taggcagggt gcattaactg tttatacggg      4260
cactgttact caaggcactg accccgttaa aacttattac cagtacactc ctgtatcatc      4320
aaaagccatg tatgacgctt actggaacgg taaattcaga gactgcgctt tccattctgg      4380
ctttaatgag gatccattcg tttgtgaata tcaaggccaa tcgtctgacc tgcctcaacc      4440
tcctgtcaat gctggcggcg gctctggtgg tggttctggt ggcggctctg agggtggcgg      4500
ctctgagggt ggcggttctg agggtggcgg ctctgagggt ggcggttccg gtggcggctc      4560
cggttccggt gattttgatt atgaaaaaat ggcaaacgct aataagggg ctatgaccga       4620 aaatgccgat gaaaacgcgc tacagtctga cgctaaaggc aaacttgatt ctgtcgctac      4680
tgattacggt gctgctatcg atggtttcat tggtgacgtt tccggccttg ctaatggtaa      4740
tggtgctact ggtgattttg ctggctctaa ttcccaaatg gctcaagtcg gtgacggtga      4800
taattcacct ttaatgaata atttccgtca atatttacct tctttgcctc agtcggttga      4860
atgtcgccct tatgtctttg gcgctggtaa accatatgaa ttttctattg attgtgacaa      4920
aataaactta ttccgtggtg tctttgcgtt tcttttatat gttgccacct ttatgtatgt      4980
attttcgacg tttgctaaca tactgcgtaa taaggagtct aataagaat tcactggccg      5040 tcgttttaca acgtcgtgac tgggaaaacc ctggcgttac ccaacttaat cgccttgcag      5100
cacatccccc tttcgccagc tggcgtaata gcgaagaggc ccgcaccgat cgcccttccc      5160
aacagttgcg cagcctgaat ggcgaatggc gcctgatgcg gtattttctc cttacgcatc      5220
tgtgcggtat ttcacaccgc atataaattg taaacgttaa tattttgtta aaattcgcgt      5280 taaattttg ttaaatcagc tcattttta accataggc cgaaatcggc aaaatccctt        5340
ataaatcaaa agaatagccc gagatagggt tgagtgttgt tccagtttgg aacaagagtc      5400
cactattaaa gaacgtggac tccaacgtca agggcgaaa aaccgtctat cagggcgatg       5460
gcccactacg tgaaccatca cccaaatcaa gtttttggg gtcgaggtgc cgtaaagcac       5520
taaatcggaa ccctaaaggg agcccccgat ttagagcttg acggggaaag ccggcgaacg      5580
tggcgagaaa ggaagggaag aaagcgaaag gagcgggcgc tagggcgctg gcaagtgtag      5640
cggtcacgct gcgcgtaacc accacacccg ccgcgcttaa tgcgccgcta cagggcgcgt      5700
actatggttg ctttgacggg tgcagtctca gtacaatctg ctctgatgcc gcatagttaa      5760 gccagcccg acacccgcca acacccgctg acgcgccctg acgggcttgt ctgctcccgg       5820
catccgctta cagacaagct gtgaccgtct ccggagctg catgtgtcag aggttttcac       5880
cgtcatcacc gaaacgcgcg a                                                5901
```

<210> SEQ ID NO 2
<211> LENGTH: 15
<212> TYPE: DNA
<213> ORGANISM: Escherichia coli

<400> SEQUENCE: 2
tgcactttag aatgt                                                     15

<210> SEQ ID NO 3
<211> LENGTH: 15
<212> TYPE: DNA
<213> ORGANISM: Escherichia coli

```
<400> SEQUENCE: 3
tgcccccgaa attgc                                                    15

<210> SEQ ID NO 4
<211> LENGTH: 15
<212> TYPE: DNA
<213> ORGANISM: Escherichia coli

<400> SEQUENCE: 4
tgcgccgcgg catgt                                                    15

<210> SEQ ID NO 5
<211> LENGTH: 15
<212> TYPE: DNA
<213> ORGANISM: Escherichia coli

<400> SEQUENCE: 5
tgcccccgaa attgc                                                    15

<210> SEQ ID NO 6
<211> LENGTH: 36
<212> TYPE: DNA
<213> ORGANISM: Escherichia coli

<400> SEQUENCE: 6
gggtgcggcc gcttccattg caggtacat atttgc                              36

<210> SEQ ID NO 7
<211> LENGTH: 39
<212> TYPE: DNA
<213> ORGANISM: Escherichia coli
<220> FEATURE:
<221> NAME/KEY: misc_feature
<222> LOCATION: (13)..(13)
<223> OTHER INFORMATION: n=a,c,t,g
<221> NAME/KEY: misc_feature
<222> LOCATION: (14)..(14)
<223> OTHER INFORMATION: n=a,c,t,g
<221> NAME/KEY: misc_feature
<222> LOCATION: (15)..(15)
<223> OTHER INFORMATION: k=t,g
<221> NAME/KEY: misc_feature
<222> LOCATION: (16)..(16)
<223> OTHER INFORMATION: n=a,c,t,g
<221> NAME/KEY: misc_feature
<222> LOCATION: (17)..(17)
<223> OTHER INFORMATION: n=a,c,t,g
<221> NAME/KEY: misc_feature
<222> LOCATION: (18)..(18)
<223> OTHER INFORMATION: k=t,g
<221> NAME/KEY: misc_feature
<222> LOCATION: (19)..(19)
<223> OTHER INFORMATION: n=a,c,t,g
<221> NAME/KEY: misc_feature
<222> LOCATION: (20)..(20)
<223> OTHER INFORMATION: n=a,c,t,g
<221> NAME/KEY: misc_feature
<222> LOCATION: (21)..(21)
<223> OTHER INFORMATION: k=t,g

<400> SEQUENCE: 7
ccgacggcat gcnnknnknn ktgcgatcca catattgcc                           39

<210> SEQ ID NO 8
<211> LENGTH: 27
<212> TYPE: DNA
<213> ORGANISM: Escherichia coli

<400> SEQUENCE: 8
```

```
ccggttaacc atgatgaaat tcgccac                                              27

<210> SEQ ID NO 9
<211> LENGTH: 28
<212> TYPE: DNA
<213> ORGANISM: Escherichia coli

<400> SEQUENCE: 9
ggaattccat atgttgtcct cttgattt                                             28
```